US010507037B2

(12) United States Patent
Doud et al.

(10) Patent No.: US 10,507,037 B2
(45) Date of Patent: Dec. 17, 2019

(54) METHOD FOR MANIPULATING CATHETER SHAFT

(71) Applicant: Covidien LP, Mansfield, MA (US)

(72) Inventors: Darren Doud, Redwood City, CA (US); Tomislav Huljev, San Carlos, CA (US); Ralph McNall, Menlo Park, CA (US); Brandon Fell, Menlo Park, CA (US); Priyanshu Gupta, Columbus, OH (US); Ryan Olivera, Fair Oaks, CA (US); Thomas C. Pham, San Jose, CA (US)

(73) Assignee: Covidien LP, Mansfield, MA (US)

( * ) Notice: Subject to any disclaimer, the term of this patent is extended or adjusted under 35 U.S.C. 154(b) by 1066 days.

(21) Appl. No.: 14/886,147

(22) Filed: Oct. 19, 2015

(65) Prior Publication Data

US 2016/0038175 A1    Feb. 11, 2016

Related U.S. Application Data

(60) Continuation of application No. 13/837,293, filed on Mar. 15, 2013, now Pat. No. 9,192,406, which is a
(Continued)

(51) Int. Cl.
*A61B 17/3207* (2006.01)
*A61M 39/10* (2006.01)
(Continued)

(52) U.S. Cl.
CPC ....... *A61B 17/320783* (2013.01); *A61M 5/34* (2013.01); *A61M 25/0014* (2013.01);
(Continued)

(58) Field of Classification Search
CPC .. A61B 17/320783; A61B 2017/00318; A61B 2017/320791; A61B 2017/00469;
(Continued)

(56) References Cited

U.S. PATENT DOCUMENTS 1,481,078 A    1/1924    Albertson
2,178,790 A    11/1939    Henry
(Continued)

FOREIGN PATENT DOCUMENTS

CA    2000621    4/1990
DE    3732236 C1    12/1988
(Continued)

OTHER PUBLICATIONS

EP17188948.8, European Search Report, dated Dec. 15, 2017, pp. 1-6.
(Continued)

*Primary Examiner* — Sarah W Aleman
*Assistant Examiner* — Rachel S Highland

(57) ABSTRACT

A catheter for performing a procedure at a treatment site in the lumen of a blood vessel. The catheter includes an elongate tubular shaft having a proximal bend, a distal bend and a hinge element. A distal portion of the shaft includes a window extending through the sidewall of the shaft between the hinge element and the distal end of the elongate tubular shaft. A working element is disposed within the lumen of the elongate tubular shaft and is configured for performing the procedure through the window at the treatment site. The bends and hinge element are configured to urge the window against a wall of the vessel at the treatment site.

12 Claims, 8 Drawing Sheets

Related U.S. Application Data division of application No. 12/578,204, filed on Oct. 13, 2009, now Pat. No. 8,414,604.

(60) Provisional application No. 61/122,601, filed on Dec. 15, 2008, provisional application No. 61/104,836, filed on Oct. 13, 2008.

(51) Int. Cl.
| | |
|---|---|
| *A61M 5/34* | (2006.01) |
| *A61M 25/00* | (2006.01) |
| *A61M 39/02* | (2006.01) |
| *A61M 25/01* | (2006.01) |
| *A61B 17/00* | (2006.01) |
| *A61B 17/22* | (2006.01) |

(52) U.S. Cl.
CPC .... *A61M 25/0097* (2013.01); *A61M 25/0152* (2013.01); *A61M 39/02* (2013.01); *A61M 39/10* (2013.01); *A61B 2017/003* (2013.01); *A61B 2017/00318* (2013.01); *A61B 2017/00331* (2013.01); *A61B 2017/00389* (2013.01); *A61B 2017/00469* (2013.01); *A61B 2017/00778* (2013.01); *A61B 2017/22038* (2013.01); *A61B 2017/320791* (2013.01); *A61M 2025/0161* (2013.01); *A61M 2039/1066* (2013.01)

(58) Field of Classification Search
CPC A61B 2017/00389; A61B 2017/00331; A61B 2017/003; A61B 2017/22038; A61B 2017/00778; A61B 2017/00371; A61B 2017/00464; A61B 2017/00477; A61M 25/0152; A61M 2025/0161; A61M 2039/1066; A61M 39/10; A61M 25/0097; A61M 39/02; A61M 5/34; A61M 25/0014; A61M 25/00; A61M 25/09; A61M 39/28; A61M 39/284; A61M 39/286; A61M 39/287; A61M 25/09041; A61M 25/02; A61M 2025/024; A61M 25/0133; A45D 2/06; A45D 2/42; A61F 2/0054; Y10T 24/3949; Y10T 24/3936; Y10T 24/3953; F16B 7/04; F16B 7/1454
USPC ........................................................ 604/250
See application file for complete search history.

(56) References Cited

U.S. PATENT DOCUMENTS

| | | | |
|---|---|---|---|
| 2,234,686 A * | 3/1941 | Walter | A61M 25/0612 27/24.1 |
| 2,701,559 A | 2/1955 | Cooper | |
| 2,850,007 A | 9/1958 | Lingley | |
| 3,064,651 A | 11/1960 | Henderson | |
| 3,082,805 A | 3/1963 | Royce | |
| 3,320,957 A | 5/1967 | Sokolik | |
| 3,614,953 A | 10/1971 | Moss | |
| 3,683,891 A | 8/1972 | Eskridge et al. | |
| 3,705,577 A | 12/1972 | Sierra | |
| 3,732,858 A | 5/1973 | Banko | |
| 3,749,085 A | 7/1973 | Wilson et al. | |
| 3,800,783 A | 4/1974 | Jamshidi | |
| 3,815,604 A | 6/1974 | O'Malley et al. | |
| 3,831,585 A | 8/1974 | Brondy et al. | |
| 3,837,345 A | 9/1974 | Matar | |
| 3,845,375 A | 10/1974 | Stiebel | |
| 3,937,222 A | 2/1976 | Banko | |
| 3,945,375 A | 3/1976 | Banko | |
| 3,976,077 A | 8/1976 | Kerfoot, Jr. | |
| 3,995,619 A | 12/1976 | Glatzer | |
| 4,007,732 A | 2/1977 | Kvavle et al. | |
| 4,020,847 A | 5/1977 | Clark, III | |
| 4,030,503 A | 6/1977 | Clark, III | |
| 4,034,744 A | 7/1977 | Goldberg | |
| 4,038,985 A | 8/1977 | Chiulli | |
| 4,112,708 A | 9/1978 | Fukuda | |
| 4,177,797 A | 12/1979 | Baylis et al. | |
| 4,210,146 A | 7/1980 | Banko | |
| 4,273,128 A | 6/1981 | Lary | |
| 4,306,562 A | 12/1981 | Osborne | |
| 4,306,570 A | 12/1981 | Matthews | |
| 4,349,032 A | 9/1982 | Koyata | |
| 4,362,156 A * | 12/1982 | Feller, Jr. | A61M 25/0637 604/165.03 |
| 4,368,730 A | 1/1983 | Sharrock | |
| 4,405,163 A * | 9/1983 | Voges | A61M 39/1011 285/305 |
| 4,424,045 A | 1/1984 | Kulischenko et al. | |
| 4,436,091 A | 3/1984 | Banko | |
| 4,445,509 A | 5/1984 | Auth | |
| 4,490,139 A | 12/1984 | Huizenga et al. | |
| 4,494,057 A | 1/1985 | Hotta | |
| 4,512,344 A | 4/1985 | Barber | |
| 4,589,412 A | 5/1986 | Kensey | |
| 4,603,694 A | 8/1986 | Wheeler | |
| 4,620,547 A | 11/1986 | Boebel | |
| 4,631,052 A | 12/1986 | Kensey | |
| 4,646,719 A | 3/1987 | Neuman et al. | |
| 4,646,736 A | 3/1987 | Auth | |
| 4,646,738 A | 3/1987 | Trott | |
| 4,649,919 A | 3/1987 | Thimsen et al. | |
| 4,653,496 A | 3/1987 | Bundy et al. | |
| 4,664,112 A | 5/1987 | Kensey et al. | |
| 4,669,469 A | 6/1987 | Gifford, III et al. | |
| 4,679,558 A | 7/1987 | Kensey et al. | |
| 4,686,982 A | 8/1987 | Nash | |
| 4,692,141 A | 9/1987 | Mahurkar | |
| 4,696,298 A | 9/1987 | Higgins et al. | |
| 4,696,667 A | 9/1987 | Masch | |
| 4,705,038 A | 11/1987 | Sjostrom | |
| 4,706,671 A | 11/1987 | Weinrib | |
| 4,728,319 A | 3/1988 | Masch | |
| 4,729,763 A | 3/1988 | Henrie | |
| 4,730,616 A | 3/1988 | Frisbie et al. | |
| 4,732,154 A | 3/1988 | Shiber | |
| 4,733,622 A | 3/1988 | DeSatnick et al. | |
| 4,745,919 A | 5/1988 | Bundey et al. | |
| 4,747,406 A | 5/1988 | Nash | |
| 4,747,821 A | 5/1988 | Kensey et al. | |
| 4,749,376 A | 6/1988 | Kensey et al. | |
| 4,754,755 A | 7/1988 | Rusted | |
| 4,757,819 A | 7/1988 | Yokoi et al. | |
| 4,765,332 A | 8/1988 | Fischell et al. | |
| 4,771,774 A | 9/1988 | Simpson et al. | |
| 4,781,186 A | 11/1988 | Simpson et al. | |
| 4,784,636 A | 11/1988 | Rydell | |
| 4,790,812 A | 12/1988 | Hawkins, Jr. et al. | |
| 4,794,931 A | 1/1989 | Yock | |
| 4,817,613 A | 4/1989 | Jaraczewski et al. | |
| 4,819,634 A | 4/1989 | Shiber | |
| 4,819,635 A | 4/1989 | Shapiro | |
| 4,838,268 A | 6/1989 | Keith | |
| 4,842,579 A | 6/1989 | Shiber | |
| 4,844,064 A | 7/1989 | Thimsen et al. | |
| 4,848,343 A | 7/1989 | Wallsten et al. | |
| 4,850,957 A | 7/1989 | Summers | |
| 4,857,046 A | 8/1989 | Stevens et al. | |
| 4,867,157 A | 9/1989 | McGurk-Burleson et al. | |
| 4,870,953 A | 10/1989 | DonMicheal et al. | |
| 4,883,458 A | 11/1989 | Shiber | |
| 4,886,061 A | 12/1989 | Fischell et al. | |
| 4,886,490 A | 12/1989 | Shiber | |
| 4,887,613 A | 12/1989 | Farr et al. | |
| 4,894,051 A | 1/1990 | Shiber | |
| 4,899,757 A | 2/1990 | Pope, Jr. et al. | |
| 4,919,133 A | 4/1990 | Chiang | |
| 4,923,462 A | 5/1990 | Stevens | |
| 4,926,858 A | 5/1990 | Gifford, III et al. | |
| 4,928,693 A | 5/1990 | Goodin et al. | |

(56) References Cited

U.S. PATENT DOCUMENTS

| | | |
|---|---|---|
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,626 A * | 7/1992 | Hilal ............... A61B 17/3462 251/149.1 |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,311 A * | 3/1995 | Walker ............... A61M 25/0668 604/160 |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,437,645 A * | 8/1995 | Urban ............... A61B 17/34 604/165.02 |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |

(56) References Cited

U.S. PATENT DOCUMENTS

| | | |
|---|---|---|
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | Mcintyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,651,771 A * | 7/1997 | Tangherlini ........ A61B 17/3462 604/158 |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,681,336 A | 10/1997 | Clement et al. |
| 5,676,697 A | 11/1997 | McDonald |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,112 A * | 8/1998 | Hart ................ A61B 17/3417 604/164.01 |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |

(56) References Cited

U.S. PATENT DOCUMENTS

| | | | |
|---|---|---|---|
| 6,048,349 | A | 4/2000 | Winston et al. |
| 6,050,949 | A | 4/2000 | White et al. |
| 6,063,093 | A | 5/2000 | Winston et al. |
| 6,066,153 | A | 5/2000 | Lev |
| 6,068,603 | A | 5/2000 | Suzuki |
| 6,068,638 | A | 5/2000 | Makower |
| 6,081,738 | A | 6/2000 | Hinohara et al. |
| RE36,764 | E | 7/2000 | Zacca et al. |
| 6,083,207 | A * | 7/2000 | Heck .............. A61M 39/06 604/160 |
| 6,095,990 | A | 8/2000 | Parodi |
| 6,099,542 | A | 8/2000 | Cohn et al. |
| 6,106,515 | A | 8/2000 | Winston et al. |
| 6,110,121 | A | 8/2000 | Lenker |
| 6,120,515 | A | 9/2000 | Rogers et al. |
| 6,120,516 | A | 9/2000 | Selmon et al. |
| 6,126,649 | A | 10/2000 | VanTassel et al. |
| 6,129,734 | A | 10/2000 | Shturman et al. |
| 6,134,003 | A | 10/2000 | Tearney et al. |
| 6,152,909 | A | 11/2000 | Bagaoisan et al. |
| 6,152,938 | A | 11/2000 | Curry |
| 6,156,046 | A | 12/2000 | Passafaro et al. |
| 6,157,852 | A | 12/2000 | Selmon et al. |
| 6,159,195 | A | 12/2000 | Ha et al. |
| 6,159,225 | A | 12/2000 | Makower |
| 6,165,127 | A | 12/2000 | Crowley |
| 6,179,859 | B1 | 1/2001 | Bates et al. |
| 6,183,432 | B1 | 2/2001 | Milo |
| 6,187,025 | B1 | 2/2001 | Machek |
| 6,190,353 | B1 | 2/2001 | Makower et al. |
| 6,191,862 | B1 | 2/2001 | Swanson et al. |
| 6,193,676 | B1 | 2/2001 | Winston et al. |
| 6,196,963 | B1 | 3/2001 | Williams |
| 6,206,898 | B1 | 3/2001 | Honeycutt et al. |
| 6,217,527 | B1 | 4/2001 | Selmon et al. |
| 6,217,549 | B1 | 4/2001 | Selmon et al. |
| 6,217,595 | B1 | 4/2001 | Shturman et al. |
| 6,221,049 | B1 | 4/2001 | Selmon et al. |
| 6,221,332 | B1 | 4/2001 | Thumm et al. |
| 6,228,049 | B1 | 5/2001 | Schroeder et al. |
| 6,228,076 | B1 | 5/2001 | Winston et al. |
| 6,231,546 | B1 | 5/2001 | Milo et al. |
| 6,231,549 | B1 | 5/2001 | Noecker et al. |
| 6,235,000 | B1 | 5/2001 | Milo et al. |
| 6,238,405 | B1 | 5/2001 | Findlay, III et al. |
| 6,241,667 | B1 | 6/2001 | Vetter et al. |
| 6,241,744 | B1 | 6/2001 | Imran et al. |
| 6,245,012 | B1 | 6/2001 | Kleshinski |
| 6,258,052 | B1 | 7/2001 | Milo |
| 6,263,236 | B1 | 7/2001 | Kasinkas et al. |
| 6,264,611 | B1 | 7/2001 | Ishikawa et al. |
| 6,266,550 | B1 | 7/2001 | Selmon et al. |
| 6,277,138 | B1 | 8/2001 | Levinson et al. |
| 6,280,190 | B1 * | 8/2001 | Hoffman .............. A61C 17/043 433/91 |
| 6,283,951 | B1 | 9/2001 | Flaherty et al. |
| 6,283,983 | B1 | 9/2001 | Makower et al. |
| 6,299,622 | B1 | 10/2001 | Snow et al. |
| 6,299,623 | B1 | 10/2001 | Wulfman |
| 6,302,875 | B1 | 10/2001 | Makower et al. |
| 6,305,834 | B1 | 10/2001 | Schubert et al. |
| 6,312,444 | B1 | 11/2001 | Barbut |
| 6,319,242 | B1 | 11/2001 | Patterson et al. |
| 6,319,275 | B1 | 11/2001 | Lashinski et al. |
| 6,330,884 | B1 | 12/2001 | Kim |
| 6,355,005 | B1 | 3/2002 | Powell et al. |
| 6,361,545 | B1 | 3/2002 | Macoviak et al. |
| 6,375,615 | B1 | 4/2002 | Flaherty et al. |
| 6,383,195 | B1 | 5/2002 | Richard |
| 6,383,205 | B1 | 5/2002 | Samson et al. |
| 6,394,976 | B1 | 5/2002 | Winston et al. |
| 6,398,798 | B2 | 6/2002 | Selmon et al. |
| 6,422,736 | B1 | 7/2002 | Antonaides et al. |
| 6,423,081 | B1 | 7/2002 | Lee et al. |
| 6,425,870 | B1 | 7/2002 | Flesch |
| 6,428,551 | B1 | 8/2002 | Hall et al. |
| 6,428,552 | B1 | 8/2002 | Sparks |
| 6,443,966 | B1 | 9/2002 | Shiu |
| 6,445,939 | B1 | 9/2002 | Swanson et al. |
| 6,447,525 | B2 | 9/2002 | Follmer et al. |
| 6,451,036 | B1 | 9/2002 | Heitzmann et al. |
| 6,454,779 | B1 | 9/2002 | Taylor |
| 6,475,226 | B1 | 11/2002 | Belef et al. |
| 6,482,217 | B1 | 11/2002 | Pintor et al. |
| 6,497,711 | B1 | 12/2002 | Plaia et al. |
| 6,501,551 | B1 | 12/2002 | Tearney et al. |
| 6,520,975 | B2 | 2/2003 | Branco |
| RE38,018 | E | 3/2003 | Anctil et al. |
| 6,532,380 | B1 | 3/2003 | Close et al. |
| 6,533,749 | B1 | 3/2003 | Mitusina et al. |
| 6,544,251 | B1 | 4/2003 | Crawford |
| 6,561,998 | B1 | 5/2003 | Roth et al. |
| 6,565,588 | B1 | 5/2003 | Clement et al. |
| 6,569,177 | B1 | 5/2003 | Dillard et al. |
| 6,592,526 | B1 | 7/2003 | Lenker |
| 6,620,180 | B1 | 9/2003 | Bays et al. |
| 6,623,437 | B2 | 9/2003 | Hinchliffe et al. |
| 6,623,495 | B2 | 9/2003 | Findlay, III et al. |
| 6,623,496 | B2 | 9/2003 | Snow et al. |
| 6,629,953 | B1 | 10/2003 | Boyd |
| 6,638,233 | B2 | 10/2003 | Corvi et al. |
| RE38,335 | E | 11/2003 | Aust et al. |
| 6,652,505 | B1 | 11/2003 | Tsugita |
| 6,652,548 | B2 | 11/2003 | Evans et al. |
| 6,656,195 | B2 | 12/2003 | Peters et al. |
| 6,666,874 | B2 | 12/2003 | Heitzmann et al. |
| 6,682,543 | B2 | 1/2004 | Barbut et al. |
| 6,733,511 | B2 | 5/2004 | Hall et al. |
| 6,740,103 | B2 | 5/2004 | Hall et al. |
| 6,746,462 | B1 | 6/2004 | Selmon et al. |
| 6,764,495 | B2 | 7/2004 | Lee et al. |
| 6,790,204 | B2 | 9/2004 | Zadno-Azizi et al. |
| 6,790,215 | B2 | 9/2004 | Findlay, III et al. |
| 6,818,001 | B2 | 11/2004 | Wulfman et al. |
| 6,830,577 | B2 | 12/2004 | Nash et al. |
| 6,843,797 | B2 | 1/2005 | Nash et al. |
| 6,849,068 | B1 | 2/2005 | Bagaoisan et al. |
| 6,863,676 | B2 | 3/2005 | Lee et al. |
| 6,911,026 | B1 | 6/2005 | Hall et al. |
| 6,970,732 | B2 | 11/2005 | Winston et al. |
| 6,997,934 | B2 | 2/2006 | Snow et al. |
| 7,104,982 | B2 * | 9/2006 | McDaniel .......... A61M 25/0097 604/533 |
| 7,153,315 | B2 | 12/2006 | Miller |
| 7,172,610 | B2 | 2/2007 | Heitzmann et al. |
| 7,208,511 | B2 | 4/2007 | Williams et al. |
| 7,235,088 | B2 | 6/2007 | Pintor et al. |
| 7,318,831 | B2 | 1/2008 | Alvarez et al. |
| 7,388,495 | B2 | 6/2008 | Fallin et al. |
| 7,479,148 | B2 | 1/2009 | Beaupre |
| 7,488,322 | B2 | 2/2009 | Brunnett et al. |
| 7,524,289 | B2 | 4/2009 | Lenker |
| 7,603,166 | B2 | 10/2009 | Casscells, III et al. |
| 7,708,749 | B2 | 5/2010 | Simpson et al. |
| 7,713,235 | B2 | 5/2010 | Torrance et al. |
| 7,713,279 | B2 | 5/2010 | Simpson et al. |
| 7,729,745 | B2 | 6/2010 | Maschke |
| 7,734,332 | B2 | 6/2010 | Sher |
| 7,753,852 | B2 | 7/2010 | Maschke |
| 7,758,599 | B2 | 7/2010 | Snow et al. |
| 7,771,444 | B2 | 8/2010 | Patel et al. |
| 7,887,556 | B2 | 2/2011 | Simpson et al. |
| 8,414,604 | B2 | 4/2013 | Doud et al. |
| 2001/0000041 | A1 | 3/2001 | Selmon et al. |
| 2001/0031784 | A1 | 10/2001 | Petersen et al. |
| 2001/0031981 | A1 | 10/2001 | Evans et al. |
| 2001/0044622 | A1 | 11/2001 | Vardi et al. |
| 2001/0049500 | A1 | 12/2001 | VanTassel et al. |
| 2002/0019644 | A1 | 2/2002 | Hastings et al. |
| 2002/0022788 | A1 | 2/2002 | Corvi et al. |
| 2002/0058904 | A1 | 5/2002 | Boock et al. |
| 2002/0077373 | A1 | 6/2002 | Hudson |
| 2002/0077642 | A1 | 6/2002 | Patel et al. |
| 2002/0095141 | A1 | 7/2002 | Belef et al. |

(56) References Cited

U.S. PATENT DOCUMENTS

| | | |
|---|---|---|
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0162544 A1 | 8/2004 | Raulerson et al. |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090801 A1* | 4/2005 | Racz ............... A61M 25/0097 604/500 |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0217687 A1 | 9/2006 | Bakos et al. |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0200980 A1* | 8/2008 | Robin ............... A61F 2/2418 623/2.11 |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 9303531 U1 | 7/1994 |
| DE | 4444166 A1 | 6/1996 |
| DE | 29722136 U1 | 5/1999 |
| EP | 0086048 A2 | 8/1983 |
| EP | 0107009 A2 | 5/1984 |
| EP | 0229620 A2 | 7/1987 |
| EP | 0291170 A1 | 11/1988 |
| EP | 0302701 A2 | 2/1989 |
| EP | 0330843 A1 | 9/1989 |
| EP | 0373927 A2 | 6/1990 |
| EP | 0421457 A1 | 4/1991 |
| EP | 0431752 A2 | 6/1991 |
| EP | 0448859 A2 | 10/1991 |
| EP | 0463798 A1 | 1/1992 |
| EP | 0490565 A1 | 6/1992 |
| EP | 0514810 A1 | 11/1992 |
| EP | 0526042 A1 | 2/1993 |
| EP | 0533320 A2 | 3/1993 |
| EP | 0608911 A1 | 8/1994 |
| EP | 0608912 A1 | 8/1994 |
| EP | 0611522 A1 | 8/1994 |
| EP | 0648414 B1 | 4/1995 |
| EP | 0657140 A1 | 6/1995 |
| EP | 0680695 B1 | 11/1998 |
| EP | 0983749 A2 | 3/2000 |
| EP | 1767159 A1 | 3/2007 |
| EP | 1875871 A2 | 1/2008 |
| GB | 2093353 A | 9/1982 |
| GB | 2115829 A | 9/1983 |
| GB | 2210965 A | 6/1989 |
| JP | 02206452 A | 8/1990 |
| JP | 2271847 A | 11/1990 |
| JP | 3186256 A | 8/1991 |
| JP | 3-210275 | 9/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 07-075611 B | 8/1995 |
| JP | 2000-225193 A1 | 8/2000 |
| SU | 442795 A1 | 9/1974 |
| SU | 665908 A1 | 6/1979 |
| WO | 89/06517 A1 | 7/1989 |
| WO | 92/07500 A2 | 5/1992 |
| WO | 9313716 A1 | 7/1993 |
| WO | 9313717 A1 | 7/1993 |
| WO | 93/16642 A1 | 9/1993 |
| WO | 9521576 A1 | 8/1995 |
| WO | 9611648 A1 | 4/1996 |
| WO | 9746164 A1 | 12/1997 |
| WO | 9804199 A1 | 2/1998 |
| WO | 9824372 A1 | 6/1998 |
| WO | 99/39648 A1 | 8/1999 |
| WO | 9952454 A1 | 10/1999 |
| WO | 00/30531 A1 | 6/2000 |
| WO | 00/54735 A1 | 9/2000 |
| WO | 00/62913 A1 | 10/2000 |
| WO | 00/68300 A1 | 11/2000 |
| WO | 00/72955 A1 | 12/2000 |

(56) References Cited

FOREIGN PATENT DOCUMENTS

| WO | 01/15609 A1 | 3/2001 |
|---|---|---|
| WO | 01/19444 A1 | 3/2001 |
| WO | 0130433 A1 | 5/2001 |
| WO | 01/43857 A1 | 6/2001 |
| WO | 0143809 A1 | 6/2001 |
| WO | 02/16017 A2 | 2/2002 |
| WO | 02/45598 A2 | 6/2002 |
| WO | 0249690 A2 | 6/2002 |
| WO | 2005123167 A1 | 12/2005 |
| WO | 2006/058223 A2 | 6/2006 |
| WO | 2006/066012 A2 | 6/2006 |

OTHER PUBLICATIONS

Brezinski et al., "Optical Coherence Tomography for Optical Biopsy," Circulation, 93: 1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

Amplatz Coronary Catheters, posted: Feb. 25, 2009, [online], [retrieved on Mar. 29, 2011], retrieved from the Cardiophile MD using Internet website <URL:http/lcardiophile.org/2009/02/amplatzcoronary-catheter.html> (3 pages).

Judkins Left Coronary Catheter, posted: Feb. 19, 2009, [online], [retrieved on Mar. 29, 2011), retrieved from the Cardiophile MD using Internet website <URL:http:/lcardiophile.org/2009/02/judkins-left-coronary-catheter.html> (3 pages).

Invitation to Pay Additional Fees dated Mar. 10, 2010 in related PCT Patent Application No. PCT/US2009/060496, 7 pages.

International Search Report dated May 3, 2010 in related International Application No. PCT/US2009/060496, 6 pages.

Written Opinion dated May 3, 2010 in related International Application No. PCT/US2009/060496, 8 pages.

Office Action dated Sep. 27, 2013 in related Japanese Application No. 2011-531255, 7 pages.

Office Action dated Nov. 4, 2014 in related Japanese Application No. 2013-272114, 6 pages.

Office Action dated May 31, 2013 in related Chinese Patent Application No. 200980146440.5, 6 pages.

Office Action dated Dec. 27, 2012 in related Chinese Patent Application No. 200980146440.5, 14 pages.

Office Action dated Aug. 11, 2015 in related Canadian Patent Application No. 2739665, 3 pages.

Patent Examination Report No. 1 dated Jun. 6, 2013 in related Australian Patent Application No. 2009303501, 4 pages.

Office Action dated Jan. 9, 2015 in related U.S. Appl. No. 13/837,293, 12 pages.

Response filed May 8, 2015 to Office Action dated Jan. 9, 2015 in related U.S. Appl. No. 13/837,293, 7 pages.

Office Action dated Jun. 20, 2012 in related U.S. Appl. No. 12/578,204, 13 pages.

Response filed Sep. 18, 2012 to Office Action dated Jun. 20, 2012 in related U.S. Appl. No. 12/578,204, 20 pages.

\* cited by examiner

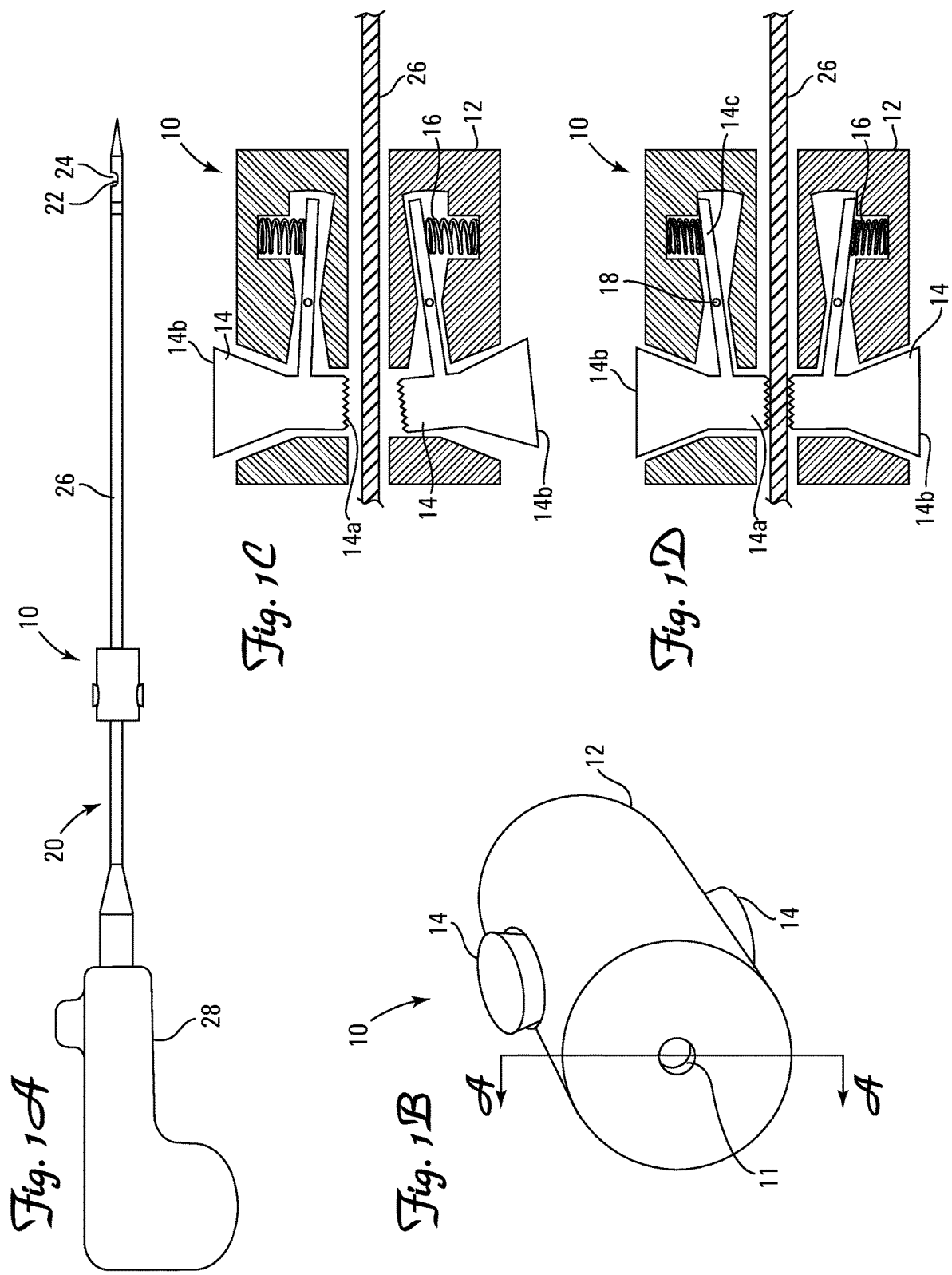

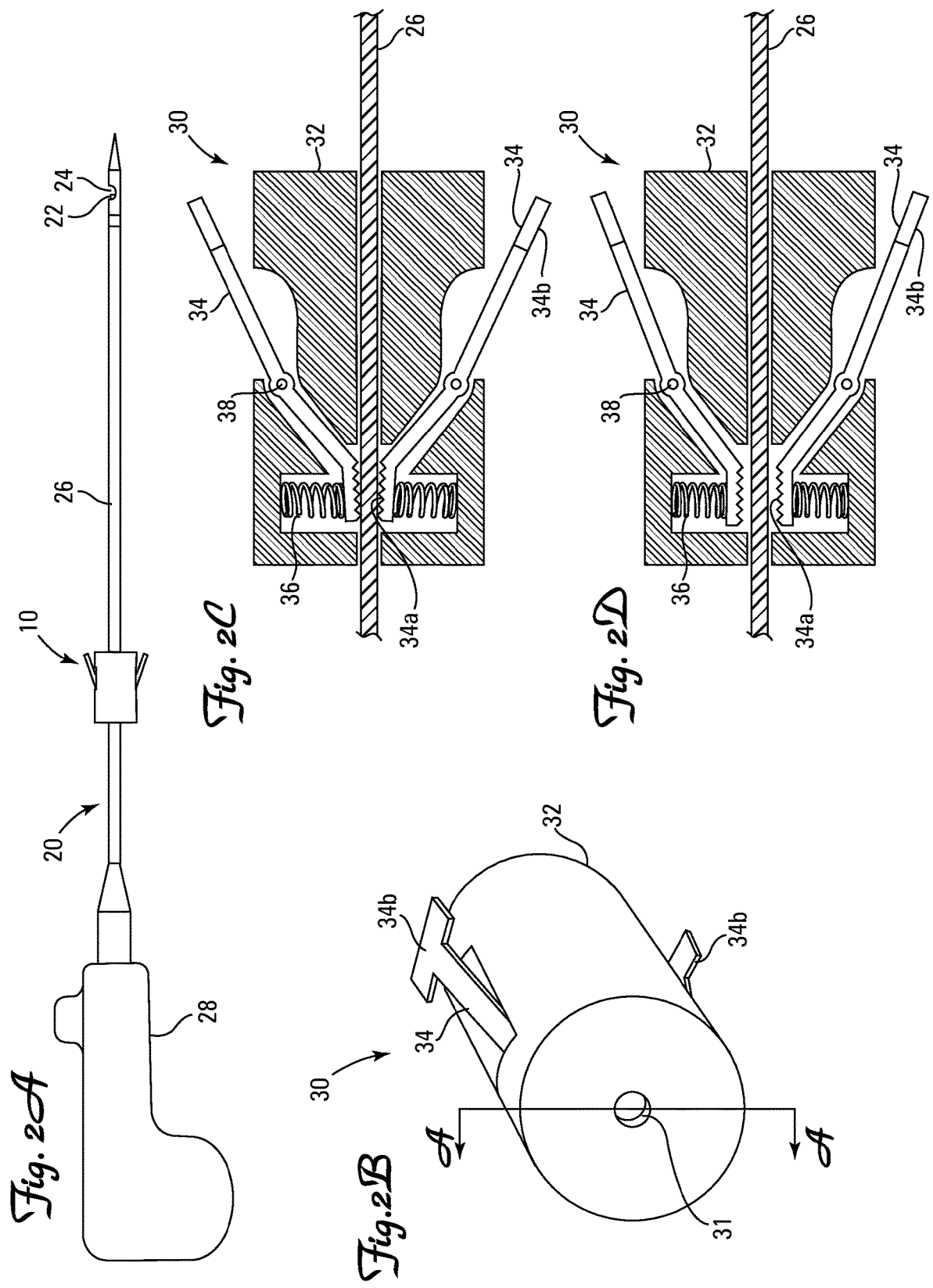

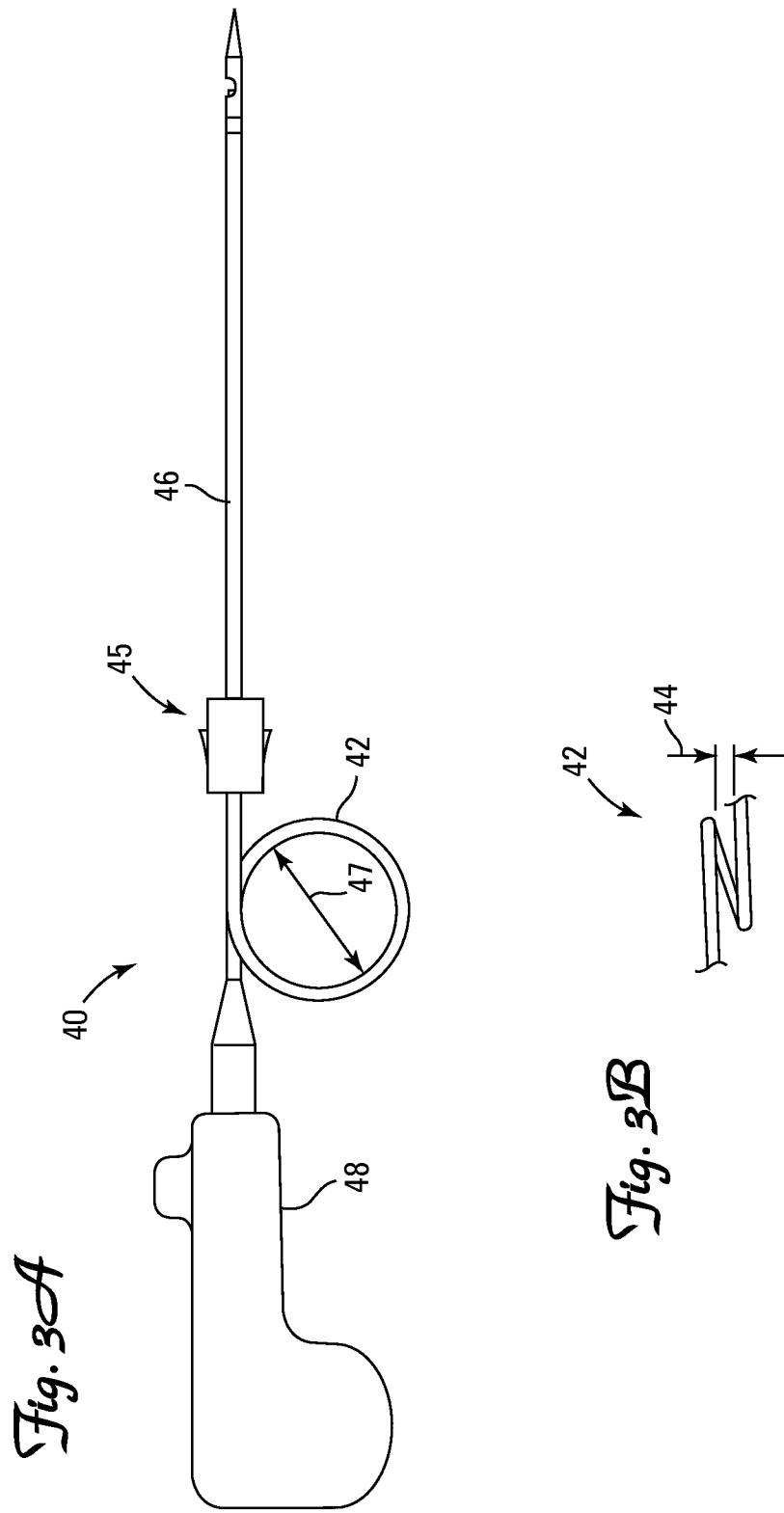

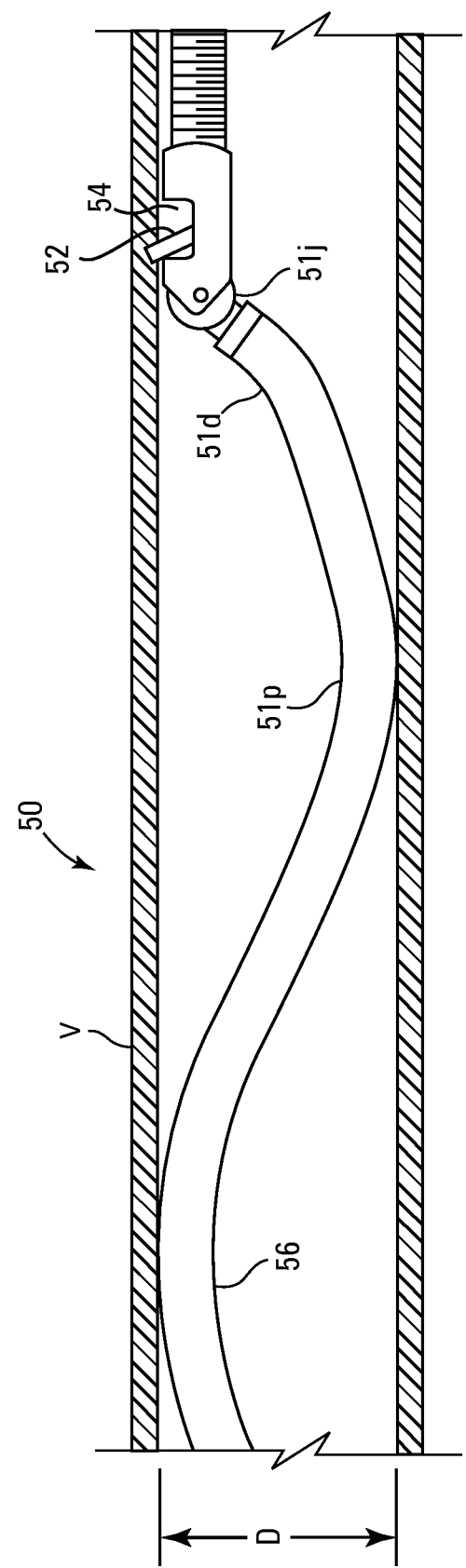

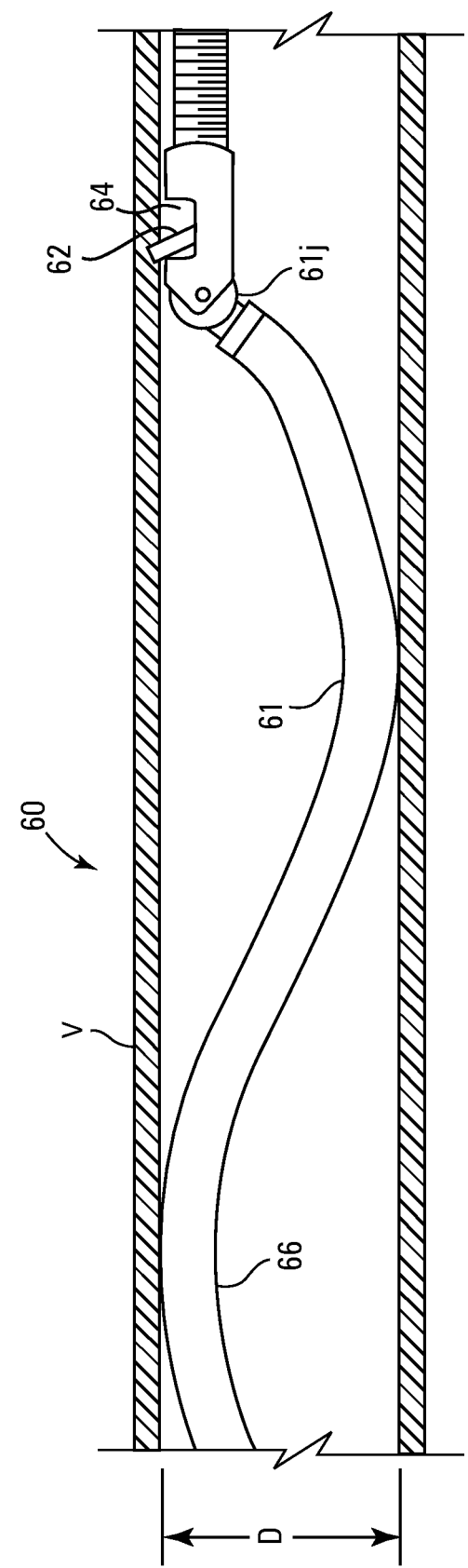

METHOD FOR MANIPULATING CATHETER SHAFT

CROSS-REFERENCE TO RELATED PATENT APPLICATIONS

The present invention claims priority to U.S. Ser. No. 13/837,293, filed Mar. 13, 2013, which is a continuation application of U.S. Ser. No. 12/578,204, filed Oct. 13, 2009, issued as U.S. Pat. No. 8,414,604, which claims priority to Provisional Application No. 61/122,601, filed on Dec. 15, 2008, and Provisional Application No. 61/104,836, filed on Oct. 13, 2008. The complete disclosure of each of the above-listed patent applications is hereby incorporated by reference for all purposes.

BACKGROUND

Atherectomy catheters are used to remove material from a blood vessel to open the lumen of the blood vessel and improve blood flow through the vessel.

Atherectomy catheters generally have cutters positioned at or near the distal end of the catheter. Some atherectomy catheters are designed to cut along only one portion of their distal circumference. Such 'directional atherectomy' catheters must be manipulated such that the cutter is positioned adjacent to the material to be cut. Such manipulation can involve urging the cutter against one side of a blood vessel so that material can be cut, and can involve rotating the proximal region of the catheter shaft so as cause rotation of the distal region of the catheter and thereby position the distally located directional cutter adjacent to material to be cut.

The present invention is directed to devices and methods for manipulating and urging a cutting element of an atherectomy catheter such that the cutter is positioned adjacent to the material to be cut.

SUMMARY

The present invention provides a manipulator which is used with an atherectomy catheter to rotate, translate, or both rotate and translate the catheter. The atherectomy catheter may have a cutting element that is able to extend through a window to cut material of interest. The manipulator can be actuated using one hand only.

In another aspect of the invention, an atherectomy catheter is provided with a pre-formed distal region. The pre-formed distal region urges the atherectomy catheter cutter into forcible contact with the inner wall of a vessel. When the cutting element encounters tissue, forces that tend to deflect the cutting element away from the tissue are resisted by the pre-formed distal region of the catheter.

In one aspect the invention is a catheter for performing a procedure at a treatment site in the lumen of a blood vessel, the blood vessel having a diameter D at the treatment site. The catheter comprises an elongate tubular shaft having distal and proximal ends and a sidewall defining a lumen, the elongate tubular shaft having a proximal bend, a distal bend and a hinge element, the proximal bend defining a first angle greater than zero, the distal bend defining a second angle greater than the first angle, the hinge element being spaced proximally of the distal end of the elongate tubular shaft and distally of the distal bend, the distal bend being positioned between the proximal bend and the hinge element, a distal portion of the elongate tubular shaft extending between the hinge element and the distal end of the elongate tubular shaft and a mid portion of the elongate tubular shaft extending between the hinge element and the proximal bend, the distal portion including a window extending through the sidewall between the hinge element and the distal end of the elongate tubular shaft. The catheter further includes a working element disposed within the lumen of the elongate tubular shaft, the working element configured for performing the procedure through the window at the treatment site, the first and second angles being selected to form a maximum excursion of the elongate tubular shaft between the proximal bend and the hinge element greater than diameter D such that the window is urged against a wall of the vessel at the treatment site. The proximal and distal bends may be configured to lie within a first plane and the hinge element may configured to permit bending of the distal portion with respect to the mid portion only in the first plane. The first and second angles may selected to urge the window against the wall of the vessel at a force in the range of about 0.05 to 0.5 pounds. The first angle may be in the range of about 90° to 150° and the second angle may be in the range of about 100° to 180°. A length from the proximal bend to the distal bend may be greater that a length from the distal bend to the hinged element. A length between the proximal and distal bends may be in the range of about 0.5 to 2.0 inches and a length between the distal bend and the hinge element may be in the range of about 0.375 to 0.625 inches. The maximum excursion may be in the range of about 3 to 40 mm.

In another aspect the invention is a catheter for performing a procedure at a treatment site in the lumen of a blood vessel. The catheter includes an elongate tubular shaft having distal and proximal ends and a sidewall defining a lumen, the elongate tubular shaft having a curved distal portion with a continuously decreasing radius of curvature, the continuously decreasing radius of curvature being oriented in a first plane from a proximal end of the distal portion to the distal end of the elongate tubular shaft, the distal portion including a hinge element spaced proximally of the distal end of the elongate tubular shaft, the hinge element dividing the distal portion into a distal segment between the hinge element and the distal end of the elongate tubular shaft and a proximal segment between the hinge element and the proximal end of the distal portion, the hinge element being configured to permit the distal segment to bend with respect to the proximal segment only in the first plane, the distal segment including a window extending through the sidewall between the hinge element and the distal end of the elongate tubular shaft. The catheter further includes a working element disposed within the lumen of the elongate tubular shaft, the working element configured for performing the procedure through the window at the treatment site, the continuously decreasing radius of curvature being selected to urge the window against a wall of the vessel at the treatment site during use. The curved distal portion may form a continuous curve in the range of about 90° to 720. A maximum curve diameter of the curved distal portion may be in the range of about 3 mm to 50 mm.

In a further aspect the invention is a method of performing a procedure at a treatment site in the lumen of a blood vessel. The method comprises providing an elongate tubular shaft having distal and proximal ends and a sidewall defining a lumen, the elongate tubular shaft having a proximal bend, a distal bend and a hinge element, the proximal bend defining a first angle greater than zero, the distal bend defining a second angle greater than the first angle, the proximal and distal bends being oriented in a first direction, the hinge element being spaced proximally of the distal end of the elongate tubular shaft and distally of the distal bend, the distal bend being positioned between the proximal bend and the hinge element, a distal portion of the elongate tubular shaft extending between the hinge element and the distal end of the elongate tubular shaft and a mid portion of the elongate tubular shaft extending between the hinge element and the proximal bend, the distal portion including a window extending through the sidewall between the hinge element and the distal end of the elongate tubular shaft The method further includes advancing the elongate tubular shaft through the lumen of the vessel to the treatment site; orienting the elongate tubular shaft in a position where the proximal and distal bends cause the distal portion of the elongate tubular shaft to bend with respect to the mid portion of the elongate tubular shaft at the hinge element in a second direction opposite the first direction to urge the window against a wall of the vessel in a desired location at the treatment site; and performing a procedure through the window at the treatment site with a working element disposed within the lumen of the elongate tubular shaft while the window is urged against the wall of the vessel. The hinge element may be configured to permit bending of the distal portion with respect to the mid portion only in the first and second directions.

In a further aspect the invention is a method of performing a procedure at a treatment site in the lumen of a blood vessel comprising providing an elongate tubular shaft having distal and proximal ends and a sidewall defining a lumen, the elongate tubular shaft having a curved distal portion with a continuously decreasing radius of curvature, the continuously decreasing radius of curvature being oriented in a first direction from a proximal end of the distal portion to the distal end of the elongate tubular shaft, the distal portion including a hinge element spaced proximally of the distal end of the elongate tubular shaft, the hinge element dividing the distal portion into a distal segment between the hinge element and the distal end of the elongate tubular shaft and a proximal segment between the hinge element and the proximal end of the distal portion, the hinge element being configured to permit the distal segment to bend with respect to the proximal segment only in the first direction and a second direction opposite the first direction, the distal segment including a window extending through the sidewall between the hinge element and the distal end of the elongate tubular shaft. The method further includes advancing the elongate tubular shaft through the lumen of the vessel to the treatment site; orienting the elongate tubular shaft in a position where the continuously decreasing radius of curvature of the curved distal portion causes the distal segment to bend with respect to the proximal segment at the hinge element in the second direction to urge the window against a wall of the vessel in a desired location at the treatment site; and performing a procedure through the window at the treatment site with a working element disposed within the lumen of the elongate tubular shaft while the window is urged against the wall of the vessel.

In another aspect the invention is a device for manipulating the shaft of a catheter comprising a body portion having a lumen sized to receive the shaft of the catheter, and a shaft engaging member having first and second shaft engaging surfaces enclosed within the body portion, the shaft engaging member having a locked position in which the first and second shaft engaging surfaces are configured to engage the shaft to lock the body on the shaft and an unlocked position in which the body is free to rotate and axially translate over the elongate tubular shaft. The shaft engaging surfaces may be biased in either the locked or the unlocked position.

In a further aspect the invention is a catheter for accessing a site on the wall of a blood vessel. The catheter includes an elongate tubular shaft having distal and proximal ends and a sidewall defining a lumen, the elongate tubular shaft having a first bend, a second bend spaced a predetermined distance distally of the first bend and a window extending through the sidewall, the window being positioned distally of the second bend and proximally of the distal end of the elongate tubular member, the first bend defining a first angle greater than zero, the second bend defining a second angle greater than the first angle, the first and second angles and the predetermined distance being selected to urge the window against the site on the wall of the blood vessel during use. The elongate tubular shaft may further include a hinge element spaced proximally of the window and distally of the second bend. Further, the catheter may include a working element disposed within the lumen of the elongate tubular shaft, the working element configured for performing a procedure through the window at the site on the wall of the blood vessel. The elongate tubular shaft may include a distal portion between the hinge element and the distal end of the elongate tubular shaft and the hinge element may be configured as a pivot point about which the distal portion bends. Further, the distal portion may have a longitudinal axis and the hinge element may be configured such that when the window is urged against the site on the wall of the blood vessel during use the distal portion is positioned such that the longitudinal axis of the distal portion is substantially parallel to a longitudinal axis of the blood vessel.

In another aspect the invention is a catheter for performing a procedure at a treatment site in the lumen of a blood vessel comprising an elongate tubular shaft having distal and proximal ends and a sidewall defining a lumen, the elongate tubular shaft having a proximal bend, a distal bend and a hinge element, the proximal bend defining a first angle greater than zero, the distal bend defining a second angle greater than the first angle, the hinge element being spaced proximally of the distal end of the elongate tubular shaft and distally of the distal bend, the distal bend being positioned between the proximal bend and the hinge element, a distal portion of the elongate tubular shaft extending between the hinge element and the distal end of the elongate tubular shaft and a mid portion of the elongate tubular shaft extending between the hinge element and the proximal bend, the distal portion including a window extending through the sidewall between the hinge element and the distal end of the elongate tubular shaft, the proximal bend, distal bend and hinge element being configured to urge the window against a wall of the vessel at the treatment site. The catheter may include a working element disposed within the lumen of the elongate tubular shaft, the working element configured for performing the procedure through the window at the treatment site when the window is urged against the wall of the blood vessel during use.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1A illustrates a schematic plan view of one embodiment of a shaft manipulator in accordance with principles of the present invention.

FIG. 1B illustrates an isometric view of the shaft manipulator illustrated in FIG. 1A.

FIGS. 1C and 1D illustrate cross sectional views along line A-A of the shaft manipulator illustrated in FIG. 1A.

FIG. 2A illustrates a schematic plan view of another embodiment of a shaft manipulator in accordance with principles of the present invention.

FIG. 2B illustrates an isometric view of the shaft manipulator illustrated in FIG. 2A.

FIGS. 2C and 2D illustrate cross sectional views along line A-A of the shaft manipulator illustrated in FIG. 2A.

FIGS. 3A and 3B illustrate schematic plan views of another embodiment of a shaft manipulator in accordance with principles of the present invention.

FIGS. 4A and 4B illustrate schematic plan views of yet another embodiment of a catheter in accordance with principles of the present invention.

FIGS. 5A to 5C illustrate schematic plan views of a further embodiment of a catheter in accordance with principles of the present invention.

DETAILED DESCRIPTION

Figure 4A:
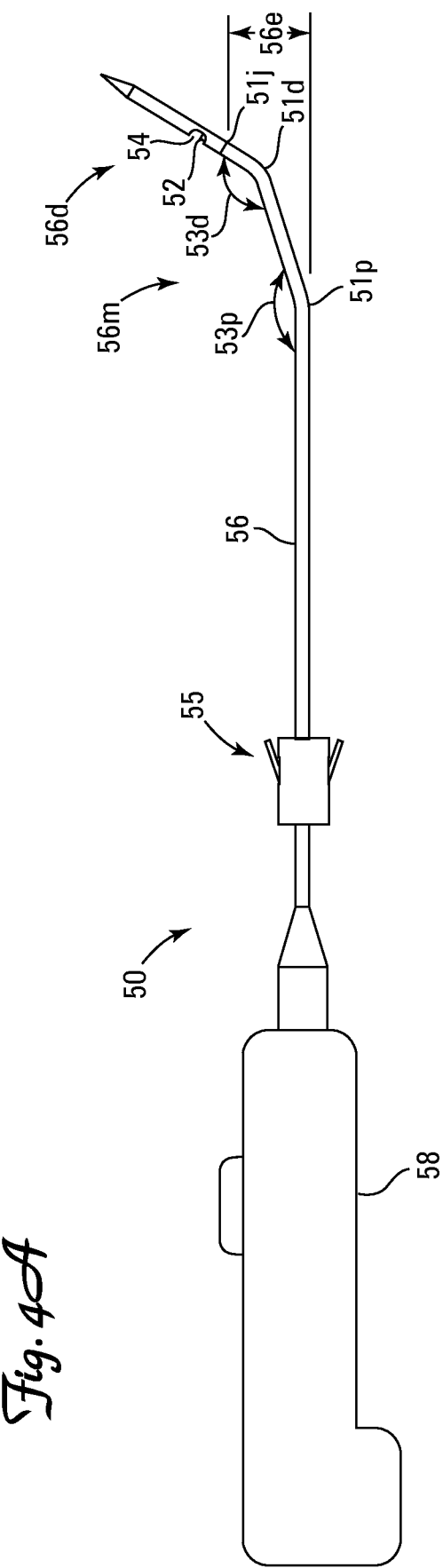

Referring to the embodiment of FIGS. 1A to 1D, the present invention is directed to a device for manipulating a catheter shaft. The invention is described in connection with an atherectomy catheter but may be used with any other catheter.

The atherectomy catheter 20 has a working element 22 such as a cutting element. The cutting element may extend through a window 24 in a shaft 26 of the catheter. As can be appreciated, the working element can be any other element such as an RF element, a visualization element or an implant delivery element. Typically catheter 20 may have a working diameter of 3 Fr to 7 Fr and have a working length of 60 cm to 180 cm.

The orientation of the working element 22 may be manipulated by rotating the shaft 26 so that a handle 28 can remain stationary while the shaft is rotated. The shaft may be rotatable in increments or may be adjustable to any angular orientation. In some embodiments the shaft is coupled to the handle in a manner which permits rotation of the shaft relative to the handle upon application of a modest torque to the shaft. In other embodiments the shaft is rotationally fixed to the handle in a manner which does not permit rotation of the shaft relative to the handle upon application of a modest torque to the shaft.

Shaft manipulator 10 is rotatably and slidably coupled to shaft 26 and configured for one-handed use. Manipulator 10 is comprised of body 12 having lumen 11, buttons 14, springs 16 and pivot pins 18. Buttons 14 are further comprised of arms 14c having holes therein for pivot pins to slidably fit through. Body 12 and buttons 14 may be made from polycarbonate, nylon, or other materials and may be injection molded or otherwise fabricated into the desired configuration. Body 12 may be molded in two halves and the halves bonded together by ultrasound, snap fit, adhesives, or other means following assembly of buttons, pivot pins and springs into body. In one embodiment two halves of body 12 are delineated by line A-A in FIG. 1B. Faces 14a, 14b of button 14 may be textured for increased friction against shaft 26 or the fingers of an operator or both. Springs 16 and pivot pins 18 may be comprised of metal such as steel, spring steel, or other metals, or engineering polymer such as polyester, liquid crystal polymer, nylon, or other polymers.

Manipulator 10 is normally in an unlocked (FIG. 1C) position with springs 16 extended so as to force faces 14a of buttons 14 away from shaft 26. The manipulator is normally unlocked to permit the user to easily move manipulator 10 to any desired position along the shaft. For example, the user may move the manipulator with one hand to an exposed, distal portion of the shaft such as a portion of the shaft near an incision or near an introducer sheath while the other hand holds the handle 28. Once the manipulator is positioned at the desired location along the shaft, rotation or translation (or both) of shaft 26 may be accomplished by pressing faces 14b of buttons 14 towards each other (FIG. 1D) with one hand of the user followed by rotation or translation (or both) of manipulator 10 with the same hand.

Use of the catheter and manipulator of FIGS. 1A to 1D is now described. Catheter 20 is introduced into the patient in any known manner. When the user desires to manipulate the catheter, the user grasps manipulator 10 and moves it to an appropriate location for manipulating the catheter. The user then locks the manipulator onto the shaft by pressing on faces 14b so as to overcome force of springs 16 and move faces 14a into frictional contact with shaft 26. The manipulator is then rotated, translated, or both to effect rotation, translation, or both of cutter 22 into contact with tissue such as atheroma. In some embodiments cutter 22 is extended outside of window 24 in a radial direction and catheter 20 is advanced through the vessel with cutter 22 extended to cut atheroma. In some embodiments atheroma is directed into interior of catheter by cutter 22.

The shaft manipulator has been described as being in a normally unlocked position, however, in other embodiments the shaft manipulator may be in a normally locked position so that the user exerts pressure on the jaws to open the jaws rather than close the jaws. FIGS. 2A to 2D illustrate shaft manipulator 30 which is configured to be in a normally locked position. Manipulator 30 is rotatably and slidably coupled to shaft 26 and configured for one-handed use. Manipulator 30 is comprised of body 32 having lumen 31, arms 34, springs 36 and pivot pins 38. Arms 34 have holes therein for pivot pins to slidably fit through, have faces 34a and have ends 34b which may be enlarged. Body 32, arms 34, faces 34a, springs 36 and pivot pins 38 may be made from materials, fabricated, and assembled substantially as described above for body 12, buttons 14, faces 14a, springs 16 and pivot pins 38 respectively.

Manipulator 30 is normally in a locked (FIG. 2C) position with springs 36 extended so as to force faces 34a of arms 34 into frictional contact with shaft 26. The manipulator is normally locked to permit the user to easily rotate or translate (or both) shaft 26. The user may move manipulator 30 with one hand to any desired position along shaft 26 by pressing arms 34b towards each other so as to force faces 34a out of contact with shaft 26 (FIG. 2D) followed by rotation or translation (or both) of manipulator 30 on shaft 26. For example, the user may move the manipulator to an exposed, distal portion of the shaft such as a portion of the shaft near an incision or near an introducer sheath. An advantage of using the manipulator is that it may be easily positioned along the shaft and manipulated with one hand while the other hand holds the handle 28.

Use of the catheter and manipulator of FIGS. 2A to 2D is now described. Catheter 20 is introduced into the patient in any known manner. When the user desires to manipulate the catheter, the user grasps manipulator 30 and unlocks the manipulator from the shaft by pressing on ends 34b so as to move faces 34a away from frictional contact with shaft 26. The user then moves manipulator 30 to an appropriate location for manipulating the catheter. Pressure on ends 34b is then removed so as to allow springs 36 to move faces 34a into frictional contact with shaft 26. The manipulator is then rotated, translated, or both to effect rotation, translation, or both of cutter 22 into contact with tissue such as atheroma. In some embodiments cutter 22 is extended outside of window 24 in a radial direction and catheter 20 is advanced through the vessel with cutter 22 extended to cut atheroma. In some embodiments atheroma is directed into interior of catheter by cutter 22.

Referring to the embodiment of FIGS. 3A and 3B, another catheter 40 is shown for use with a manipulator 45. Catheter 40 may be similar to catheter 20 described above but may be any other catheter with a working element, having shaft 46 similar to shaft 26 described above or another shaft, in any case with the addition of loop 42. Manipulator 45 may be comprised of manipulator 10, 30 described above or may be another manipulator. Handle 48 may be similar to handle 28 described above but may be any other handle.

Catheter 40 includes shaft 46 having a loop 42 positioned between the manipulator and the handle. Loop 42 may be formed of a flexible catheter portion which is designed to form the loop when the shaft is manipulated or may be a pre-shaped loop catheter portion, and when formed is comprised of gap 44. Shaft 46 is fixedly coupled to handle 48 so that the shaft does not rotate or translate relative to handle. When manipulator 45 is rotated or translated, loop 42 is flexible enough to permit the distal portion of the shaft to be rotated or translated by the manipulator without requiring a change in the orientation or position of the handle. During rotation or translation of shaft 46 relative to handle 48 loop 42 may become larger or smaller in diameter 47 and gap 44 may increase or decrease, or both, to accommodate rotation or translation of shaft 46 while allowing handle 48 to remain in an unchanged position.

Use of the catheter of FIGS. 3A and 3B is now described. The catheter is introduced into the patient in any known manner. When the user desires to manipulate the catheter, the user grasps the manipulator and moves it to an appropriate location for manipulating the catheter. The user then locks the manipulator onto the shaft. As the shaft is manipulated, the loop will constrict, expand, or change gap as necessary to accommodate rotation, translation, or both of the shaft while the handle position remains unchanged. In some embodiments cutter 22 is extended outside of window 24 in a radial direction and catheter 20 is advanced through the vessel with cutter 22 extended to cut atheroma. In some embodiments atheroma is directed into interior of catheter by cutter 22.

FIGS. 4A and 4B illustrate another catheter 50 for use with a manipulator 55. A distal portion of the shaft is shaped to provide an apposition force to urge the cutting element against the vessel wall. Catheter 50 may be similar to catheter 20 described above but may be any other catheter with a working element, having shaft 56 similar to shaft 26 described above or another shaft, in any case with the addition of jog 51j and preformed bends 51p, 51d. Catheter 50 is also comprised of working element 52 and window 54 which may be similar in construction, materials, and function as working element 22 and window 24 respectively. The window 54 is positioned at a radially inner position on the shaft so that the working element 52 is urged against the vessel wall when the catheter is positioned within a vessel. Jog 51j and preformed bends 51p, 51d cooperate to urge working element 52 into contact with material to be cut in a vessel. Manipulator 55 may be comprised of manipulator 10, 30 described above or may be another manipulator. Use of manipulator 55 with catheter 50 is optional. Handle 58 may be similar to handle 28 described above but may be any other handle.

Catheter shaft 56 includes jog 51j and preformed bends 51p, 51d. Jog 51j is comprised of a hinge structure that allows distal portion 56d of shaft 56 to abruptly bend in relation to mid portion 56m of shaft 56. Catheter structures capable of jog are further described in U.S. patent application Ser. No. 10/896,741, filed Jul. 21, 2004 and published as US 2005/0177068 A1, paragraphs [0092] to [0094], [0100] to [0102], to [0107] and FIGS. 1, 1A, 2, 4A and 4B. The entire contents of US Patent Publication US 2005/0177068 are hereby incorporated herein in their entirety. In one embodiment the preformed bends are formed such that the mid portion and the portion of the catheter shaft proximal of the mid portion lie within a first plane and the hinge element is configured to permit bending of the distal portion with respect to the mid portion only in the first plane. Preformed bends 51p, 51d may be formed by constraining distal portion 56d in metal molds followed by application of heat to cause catheter 56 to take the shape of the mold, or other means as are known to those of skill in the art. Preformed bend 51p has a lesser angle 53p than preformed bend 51d angle 53d. Preformed bend 51p angles of 90 to 150 degrees are contemplated. In one embodiment preformed bend 51p angles are 100 to 120 degrees. In other embodiments angle 53p are 95, 105, 110, 115, 125, 130 or 140 degrees. Preformed bend 51d angles 53d of 100 to 180 degrees are contemplated. In one embodiment preformed bend 51d angles are 120 to 140 degrees. In other embodiments angle 53d is 110, 130, 150, 160, or 170 degrees. The length from preformed bend 51p to preformed bend 51d is generally greater than the length from preformed bend 51d to jog 51j. Lengths from preformed bend 51p to preformed bend 51d of 0.5 to 2.0 inches are contemplated. In one embodiment length from preformed bend 51p to preformed bend 51d is 1.00 to 1.25 inches. In other embodiments lengths from preformed bend 51p to preformed bend 51d are 0.75, 1.5 or 1.75 inches. Lengths from preformed bend 51d to jog 51j of 0.125 to 1.0 inches are contemplated. In one embodiment length from preformed bend 51d to jog 51e is 0.375 to 0.625 inches. In some embodiments lengths from preformed bend 51d to jog 51j are 0.25, 0.5, 0.75 or 0.875 inches. The combined bends 51d, 51p and lengths between bends and between bend and jog cause catheter 56 to have a maximum excursion 56e from the unbent portion of catheter 56 to jog 56j. Generally, catheters of the invention are chosen to have an excursion greater than the diameter of the vessel or conduit that catheter 50 will be used within. Excursions 56e of 3 to 40 millimeters are contemplated. In one embodiment excursion 56e is 5 to 8 mm. In some embodiments excursions 56e are 4, 5, 6, 7, 8, 10, 12, 15, 20, 25, 30 or 35 millimeters.

When catheter 50 is positioned inside a vessel V of diameter D less than unconstrained excursion 56e, preformed bends 51p and 51d are forced to assume angles larger than their undeflected preformed angles while jog 51j allows distalmost portion of catheter 50 to become oriented along inner wall of vessel V. This cooperation between jog 56j and bends 51p, 51d forces or urges window 54 into contact with inner wall of vessel V as preformed bends attempt to restore their undeflected preformed angles. Preformed bend 51d maintains apposition force of cutter 52 and window 54 against the inner wall of vessel V at the low end of vessel diameters. As vessel diameter increases preformed bend 51p eventually starts to apply apposition force to the catheter tip as well. Urge forces of 0.05 to 0.5 lbs are contemplated. In one embodiment the urge force is 0.1 lbs. In some embodiments the urge force is 0.075, 0.2, 0.3 or 0.4 lbs. Working element 52, such as a cutter, can be extended through window 54 to contact material to be cut, such as atheroma. During cutting, cutting forces tending to deflect cutter away from inside surface of vessel will be resisted by the urge forces produced as described above. The distal portion of shaft 56 can be rotated, translated, or both by manipulator 55 (if used) to assure that window 54 is circumferentially oriented so as to contact the material to be cut.

Use of the catheter of FIGS. 4A and 4B is now described. A catheter 50 having excursion 56e greater than the inside diameter of vessel V is chosen. Optionally, the catheter is introduced over a guidewire into the patient in any known manner to a location in vessel V where material is to be removed. The catheter, when introduced over a guidewire, tends to straighten somewhat and follow the guidewire to the location. Preformed bends 51p, 51d in cooperation with jog 51j urge window 54 against inner wall of vessel V. In some embodiments cutter 52 is extended outside of window 54 in a radial direction and catheter 50 is advanced through the vessel with cutter 52 extended to cut atheroma. In some embodiments atheroma is directed into interior of catheter by cutter 52. Optionally, when the user desires to manipulate the catheter, the user grasps manipulator 55 and moves it to an appropriate location for manipulating the catheter. The user then locks the manipulator onto shaft 56 and rotates, translates, or both the shaft while handle 58 position remains unchanged.

Figure 5A:
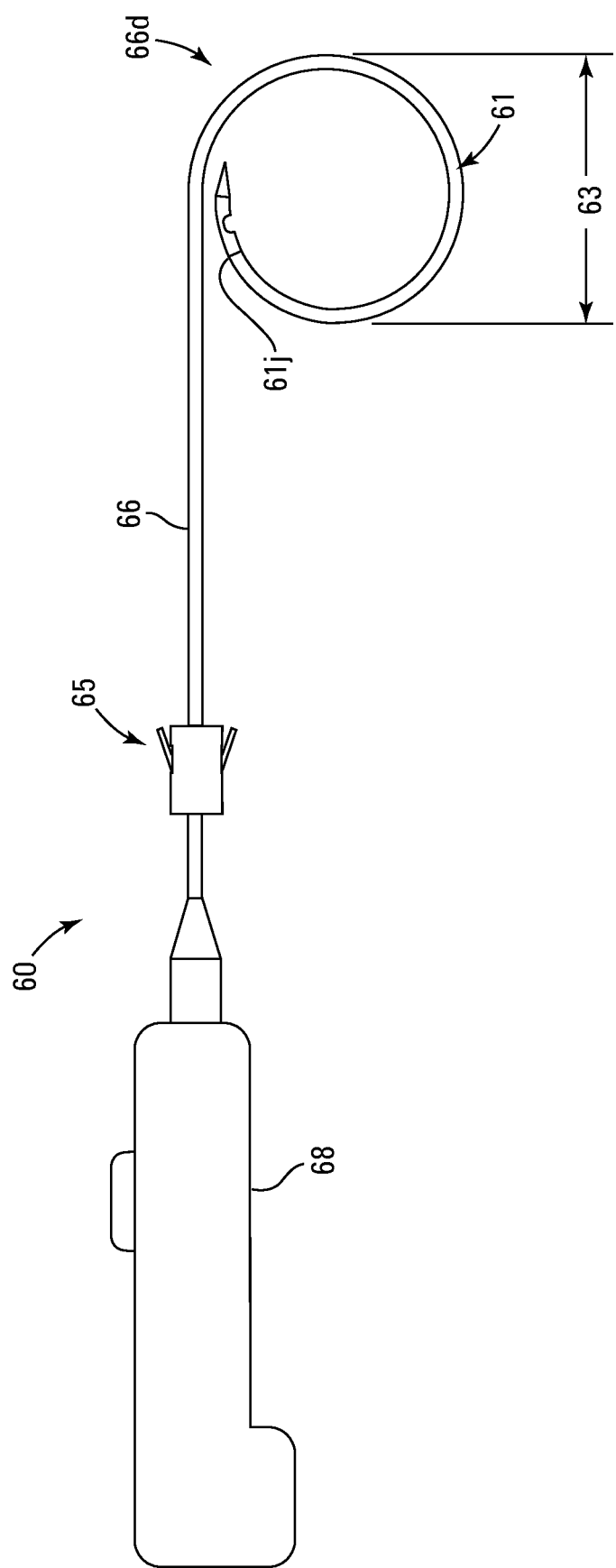
Figure 5B:
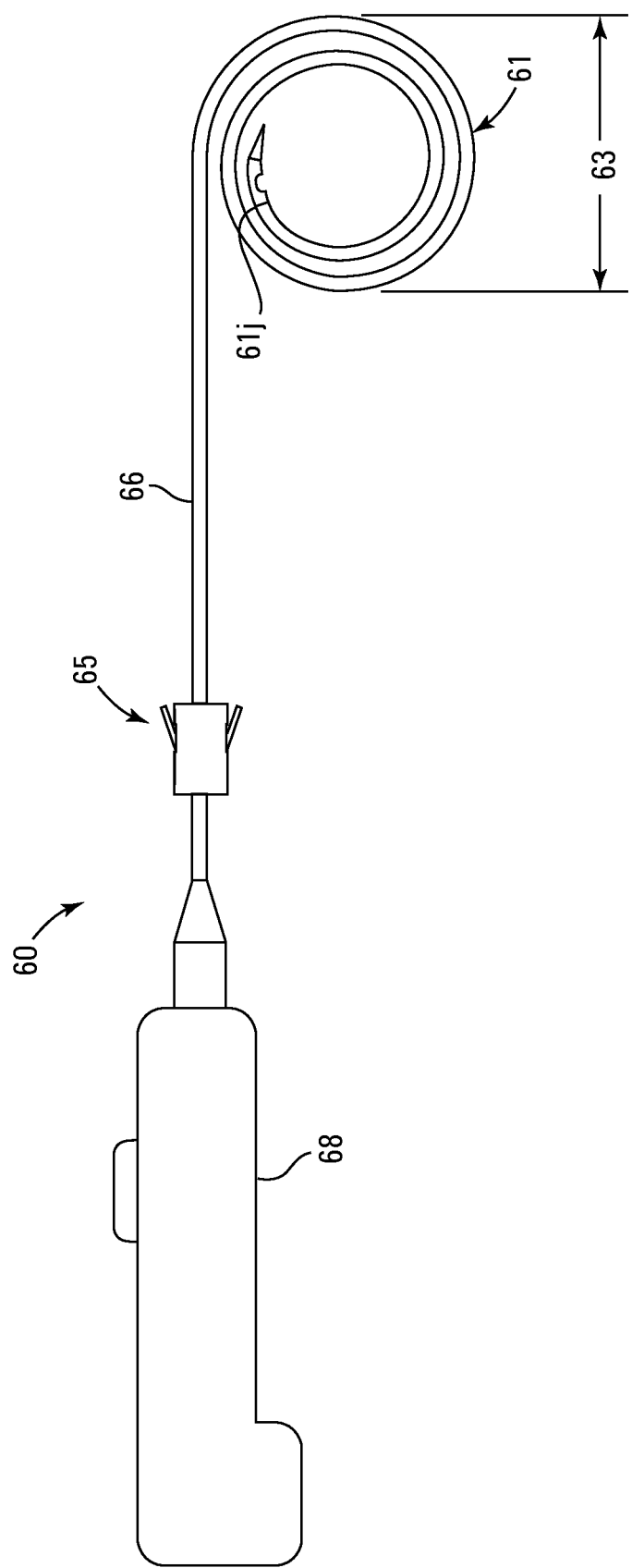

FIGS. 5A to 5C illustrate another catheter 60 for use with a manipulator 65. A distal portion of the shaft is shaped to provide an apposition force to urge the cutting element against the vessel wall. Catheter 60 may be similar to catheter 20 described above but may be any other catheter with a working element, having shaft 66 similar to shaft 26 described above or another shaft, in any case with the addition of jog 61j and continuously decreasing radius curve 61. Jog 61j may be similar in construction, materials, and function to jog 51j. Catheter 60 is also comprised of working element 62 and window 64 which may be similar in construction, materials, and function as working element 22 and window 24 respectively. Working element 62 is positioned at a radially inward position on the shaft so that the working element 62 is urged against the vessel wall when the catheter is positioned within a vessel. Jog 61j and continuously decreasing radius curve 61 cooperate to urge working element 62 into contact with material to be cut in a vessel. Manipulator 65 may be comprised of manipulator 10, 30 described above or may be another manipulator. Use of manipulator 65 with catheter 60 is optional. Handle 68 may be similar to handle 28 described above but may be any other handle.

Catheter shaft 66 includes jog 61j and continuously decreasing radius curve 61. Continuously decreasing radius curve 61 may be formed by constraining distal portion 66d of catheter shaft 66 in metal molds followed by applying heat to cause distal portion 66d to take the shape of the mold, or other means as are known to those of skill in the art. Distal portion 66d may curl around at least 90 degrees up to at least 720 degrees. FIG. 5A shows the shaft curling about 360 degrees and FIG. 5B shows the shaft curling about 720 degrees. In other embodiments distal portion 66d curls around 120, 150, 180, 240, 300, 480, or 600 degrees. The maximum curve diameter 63 may vary from 3 mm to 50 mm although the maximum curve diameter may be outside this range depending upon the particular application. In one embodiment the maximum curve diameter is 10 to 12 mm. In other embodiments the maximum curve diameter is 4, 6, 8, 15, 20, 25, 30, or 40 mm.

In another embodiment, the continuously decreasing radius curve 61 may be comprised of a number of discrete preformed bends (not shown). As can be appreciated, the number of sections of decreasing radius may vary. For example, catheters having from 2 to 100 sections are contemplated. In other embodiments, the catheter may have 4, 6, 8, 10, 15, 20, 40, 60, 75, or 100 sections. In yet another embodiment, catheter has an infinite number of sections as disclosed by the continuously variable embodiment of FIGS. 5A to 5C.

The continuously decreasing radius is intended to provide a relatively uniform apposition force over a range of vessel diameters. Of course, the actual apposition force may vary considerably during use since vessel geometry and size vary considerably from patient to patient; however, the shape of the shaft tends to provide a uniform force over a range of vessel sizes.

When catheter 60 is positioned inside a vessel V of diameter D less than maximum curve diameter 63, the continuously decreasing radius curve 61 is forced to increase in diameter while jog 61j allows distalmost portion of catheter 60 to become oriented along inner wall of vessel V. This cooperation between jog 56j and curve 61 forces or urges window 64 into contact with inner wall of vessel V as curve 61 attempts to restore its undeformed diameter. Working element 62, such as a cutter, can be extended through window 64 to contact material to be cut, such as atheroma. During cutting, cutting forces tending to deflect cutter away from inside surface of vessel will be resisted by the urge forces produced as described above. The distal portion of shaft 66 can be rotated, translated, or both by manipulator 65 (if used) to assure that window 64 is circumferentially oriented so as to contact material to be cut.

Use of the catheter of FIGS. 5A to 5C is now described. The catheter is introduced over a guidewire into the patient in any known manner to a location where material is to be removed. The catheter, when introduced over a guidewire, tends to straighten somewhat and follow the guidewire to the location. Curve 61 in cooperation with jog 61j urge window 64 against inner wall of vessel V. In some embodiments cutter 62 is extended outside of window 64 in a radial direction and catheter 60 is advanced through the vessel with cutter 62 extended to cut atheroma. In some embodiments atheroma is directed into interior of catheter by cutter 62. Optionally, when the user desires to manipulate the catheter, the user grasps manipulator 65 and moves it to an appropriate location for manipulating the catheter. The user then locks the manipulator onto the shaft 66 and rotates, translates, or both the shaft while handle 68 position remains unchanged.

The present invention has been described in connection with preferred embodiments but may, of course, be practiced while departing from the above described illustrative embodiments.

What is claimed is:

1. A device for manipulating the shaft of a catheter comprising:

a body portion having a lumen sized to receive the shaft of the catheter such that the shaft of the catheter extends lengthwise through the lumen and proximal and distal end portions of the shaft protrude from opposite ends of the body portion;

a first arm connected to the body portion for rotation about a first pivot axis with respect to the body portion, the first arm comprising a first shaft engaging surface enclosed within the body portion and configured to rotate with the first arm about the first pivot axis; and a second arm connected to the body portion for rotation about a second pivot axis with respect to the body portion, the second arm comprising a second shaft engaging surface enclosed within the body portion and configured to rotate with the second arm about the second pivot axis, wherein the first and second arms have a locked position in which the first and second arms are oriented about the first and second pivot axes such that the first and second shaft engaging surfaces are configured to engage the shaft of the catheter to lock the body portion on the shaft, and an unlocked position in which the first and second arms are oriented such that at least one of the first and second shaft engaging surfaces is configured to be disengaged from the shaft of the catheter so that the body portion is free to rotate and axially translate over the shaft of the catheter.

2. The device of claim 1 wherein the shaft engaging surfaces are biased toward the unlocked position.

3. The device of claim 2 further comprising at least one spring biasing the shaft engaging surfaces toward the unlocked position.

4. The device of claim 1 further comprising at least one button accessible on the body portion for moving the first and second arms to the locked and unlocked positions.

5. The device of claim 4 wherein the at least one button comprises first and second buttons accessible outside the body portion, the first and second buttons being configured to be depressed relative to the body portion to rotate the respective first and second arms about the first and second pivot axes.

6. The device of claim 1 wherein the shaft engaging surfaces are biased toward the locked position.

7. The device of claim 6 further comprising at least one spring biasing the shaft engaging surfaces toward the locked position.

8. The device of claim 7 further comprising at least one button configured to move the first and second arms to the locked and unlocked positions.

9. The device of claim 1 in combination with the catheter, wherein the device is received on the shaft of the catheter.

10. The device in combination with the catheter as set forth in claim 9, wherein the catheter includes a handle coupled to the shaft of the catheter, wherein the catheter is rotatable relative to the handle.

11. The device in combination with the catheter as set forth in claim 9, wherein the catheter includes a cutter configured to remove material from a body lumen.

12. The device of claim 1, wherein the body portion has a length and the body portion is free to axially translate over the shaft of the catheter body along an axial distance that is greater than the length of the body portion.

\* \* \* \* \*